United States Patent [19]

Zaiger et al.

[11] Patent Number: Plant 8,442

[45] Date of Patent: Nov. 2, 1993

[54] PEACH TREE "SUGAR GIANT"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 8,475

[22] Filed: Jan. 25, 1993

[51] Int. Cl.[5] ..... A01H 5/00

[52] U.S. Cl. ..... Plt./42.1

[58] Field of Search ..... Plt./42.1

[56] References Cited

U.S. PATENT DOCUMENTS

P.P. 8,085 1/1993 Zaiger et al. ..... Plt. 42.1

*Primary Examiner*—James R. Feyrer

[57] ABSTRACT

A new and distinct variety of peach tree with the following unique combination of desirable features.

1. Heavy and regular production of fruit.
2. Relatively uniform large fruit throughout the tree.
3. Fruit with firm white flesh.
4. Fruit with good handling and shipping quality.
5. Vigorous upright growth.
6. Producing mild, sweet, sub-acid fruit with good flavor and eating quality.
7. An attractive fruit having a white ground color with a light red blush.

1 Drawing Sheet

ORIGIN OF THE VARIETY

The present new variety of peach tree was originated by us in the experimental orchard located near Modesto, Calif. from a first generation cross between two selected seedlings with the field identification numbers of 18EA213 and 51GA205. The female parent with the identification number 18EA213 originated from a cross between a nectarine seedling of unknown parentage and Royal Gold Peach (U.S. Plant Pat. No. 2,663). The pollen parent with the identification number 51GA205 originated from a first generation cross between a selected seedling from an open pollinated O'Henry Peach (U.S. Plant Pat. No. 2,964) crossed with a selected seedling originating from a cross between an open pollinated May Grand Nectarine (U.S. Plant Pat. No. 2,794) seedling crossed with Sam Houston Peach (non-patented). (Royal Gold Peach is classified as a yellow flesh peach, it originated as a bud mutation from the white flesh Springtime Peach (U.S. Plant Pat. No. 1,268) and carries a factor for white flesh). A large group of these first generation seedlings were planted and maintained under careful observation by us, during which time one such seedling, which is the present variety, having especially desirable fruit characteristics was selected for asexual reproduction and commercialization.

ASEXUAL REPRODUCTION OF THE VARIETY

The present new and distinct variety of peach tree was asexually reproduced by budding, as performed by us in our experimental orchard located near Modesto, Calif. and shows that all characteristics run true to the original tree and are established and transmitted in succeeding propagations.

SUMMARY OF THE VARIETY

The new and distinct variety of peach tree is of large size, vigorous, upright growth and a heavy and regular bearer of large, freestone fruit with good flavor and eating quality. The tree is further characterized by producing relatively uniform, large, firm, white flesh fruit with good handling and shipping quality and in comparison to the Giant Babcock Peach (U.S. Plant Pat. No. 1,353) the fruit of the new variety has firmer flesh, greater handling and shipping quality, and is approximately one week earlier in maturity.

DESCRIPTION OF THE PHOTOGRAPHS

The accompanying color photographic illustrations show typical specimens of the foliage and fruit of the present new variety of peach tree.

The upper and lower surface of the leaves being illustrated with an exterior and sectional view of the fruit divided in the suture plane to reveal flesh coloration, pit cavity and showing a stone remaining in place.

The photographs were taken shortly after being picked at maturity (shipping ripe) and the colors are as nearly true as is reasonably possible in a color representation of this type.

DESCRIPTION OF THE VARIETY

The following is a detailed botanical description of the new and distinct variety of peach tree, its flowers, foliage and fruit as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Medium.
- *Texture.*—Medium shaggy.
- *Color.*—Brown to grayish brown (6-E-2) to (6-E-4).

Branches:
- *Size.*—Medium.
- *Texture.*—Smooth to medium rough; varies with maturity.
- *Lenticels.*—Medium size. Medium number.

*Color.*—Light brown to brown—varies with maturity.

Leaves:

*Size.*—Large. Average length — $5\frac{3}{4}''$ to $6\frac{1}{4}''$. Average width — $1\frac{1}{2}''$ to $1\frac{7}{8}''$.

*Form.*—Lanceolate — pointed.

*Thickness.*—Medium.

*Margin.*—Crenate.

*Petiole.*—Medium length. Medium thickness.

*Texture.*—Smooth.

*Glands.*—Number varies from 0 to 4. Average Number 2. Reniform. Medium size. Located on base of leaf blade and upper portion of petiole.

*Color.*—Upper surface — green to dark green (27-E-6) to (27-F-7). Lower surface — light green to green (27-E-3) to (27-E-4).

Flower Buds:

*Size.*—Medium to large.

*Form.*—Plump.

*Pubescence.*—Pubescent.

Flowers:

*Size.*—Large — showy.

*Blooming period.*—Mar. 1, 1992 to Mar. 7, 1992. Varies slightly with climatic conditions.

*Pollen.*—Present.

*Color.*—Pink.

Fruit:

*Maturity when described.*—Shipping ripe.

*Date of first picking.*—Jul. 4, 1992.

*Date of last picking.*—Jul. 9, 1992.

*Size.*—Large. Average diameter axially — 3" to $3\frac{1}{4}''$. Average transversely in suture plane — 3" to $3\frac{1}{4}$.

*Form.*—Nearly Globose, slightly irregular on suture plane, with slight tip at apex and slightly flattened at stem end.

*Suture.*—Shallow but pronounced — extends from base to apex.

*Ventral surface.*—Lipped — slightly enlarged.

*Cavity.*—Rounded — slightly elongated in suture plane. Average depth — $\frac{5}{8}''$. Average breadth — $\frac{7}{8}''$.

*Base.*—Retuse.

*Apex.*—Short — usually slight pistil point — varies from rounded to slight point.

Skin:

*Thickness.*—Medium.

*Texture.*—Medium — tenacious to flesh.

*Tendency to crack.*—None.

*Down.*—Moderate amount. Medium in length.

*Color.*—White to pinkish white ground color (7-A-1) to (7-A-2) partially overspread with light red to pale red blush (11-A-5) to (11-A-7).

Flesh:

*Ripens.*—Evenly.

*Texture.*—Firm.

*Fibers.*—Few, small, tender.

*Juice.*—Moderate.

*Aroma.*—Moderate.

*Amygdalin.*—Undetected.

*Flavor.*—Good — mild, sweet, sub-acid.

*Eating quality.*—Good.

*Color.*—White (11-A-1). Pit cavity red to violet red (11-A-8) to (12-A-8) with slight bleeding of red into flesh surrounding pit cavity, heavier near apex.

Stone:

*Type.*—Freestone.

*Size.*—Large. Average length — $1\frac{7}{8}''$. Average width — 1 3/16". Average thickness — $\frac{5}{8}''$.

*Form.*—Obovate.

*Base.*—Usually straight — varies from round to straight.

*Apex.*—Varies from rounded to cuspidate.

*Surface.*—Irregularly furrowed toward apex, pitted toward base. Pit cavities vary from elongated to round.

*Ridges.*—Rounded.

*Sides.*—Equal to unequal.

*Tendency to split.*—None.

*Color.*—Brown to reddish brown (9-D-7) to (10-D-8).

Use: Dessert.

*Market.*—local and long distance.

Keeping quality: Good.

Shipping quality: Good.

The present new variety of peach tree, its flowers, foliage and fruit herein described may vary in slight detail due to climatic, soil conditions and cultural practices under which the variety may be grown. The present botanical description is that of the new variety grown under the ecological conditions prevailing near Modesto, Calif.

We claim:

1. A new and distinct variety of peach tree, substantially as illustrated and described, which is of large size, vigorous, upright growth and a productive and regular bearer of large, white flesh, freestone fruit with good flavor and eating quality; the fruit is further characterized by being relatively uniform in size throughout the tree, having good handling and shipping quality and having an attractive red blush.

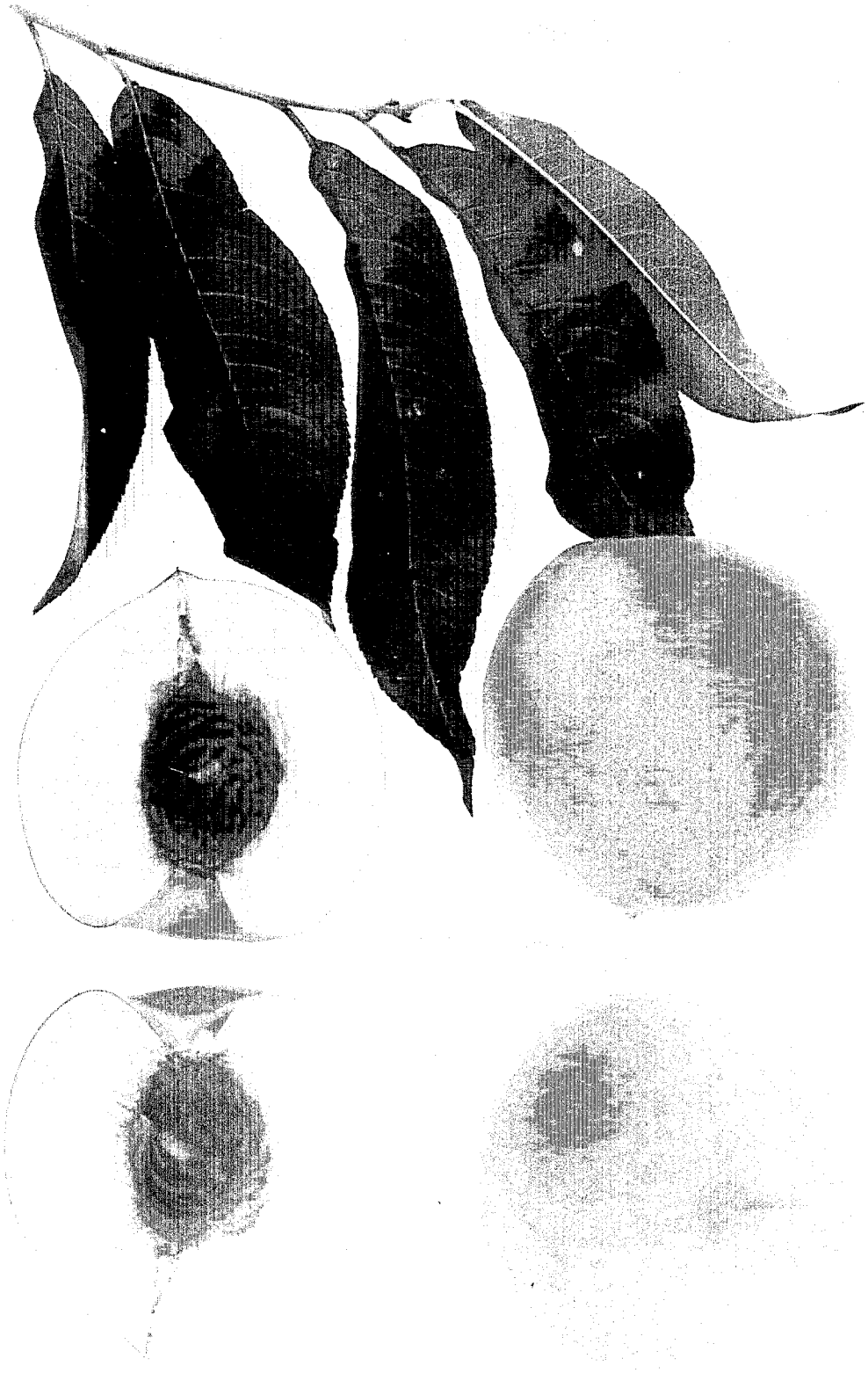

* * * * *